(12) United States Patent
Brock et al.

(10) Patent No.: US 7,744,622 B2
(45) Date of Patent: Jun. 29, 2010

(54) SURGICAL INSTRUMENT

(75) Inventors: David L. Brock, Natick, MA (US);
Woojin Lee, Cambridge, MA (US)

(73) Assignee: Hansen Medical, Inc., Mountain View, CA (US)

( * ) Notice: Subject to any disclaimer, the term of this patent is extended or adjusted under 35 U.S.C. 154(b) by 309 days.

(21) Appl. No.: 10/977,796

(22) Filed: Oct. 29, 2004

(65) Prior Publication Data
US 2005/0228440 A1 Oct. 13, 2005

Related U.S. Application Data

(63) Continuation of application No. 09/783,637, filed on Feb. 14, 2001, now abandoned, which is a continuation of application No. PCT/US00/12553, filed on May 9, 2000.

(60) Provisional application No. 60/133,407, filed on May 10, 1999.

(51) Int. Cl.
*A61B 17/28* (2006.01)
(52) U.S. Cl. .................................... 606/205
(58) Field of Classification Search ................ 600/407, 600/102, 103, 104, 109, 427, 114, 118, 106, 600/117; 901/2, 4, 36; 700/65, 83, 85, 264; 606/1, 130, 205, 147, 170, 167, 144, 174
See application file for complete search history.

(56) References Cited

U.S. PATENT DOCUMENTS

| | | | |
|---|---|---|---|
| 2,978,118 A | 4/1961 | Goertz et al. | |
| 3,923,166 A | 12/1975 | Fletcher et al. | |
| 4,604,016 A | 8/1986 | Joyce | |
| 4,750,475 A | 6/1988 | Yoshihashi | |
| 4,853,874 A | 8/1989 | Iwamoto et al. | |
| 4,930,494 A | 6/1990 | Takehana et al. | |
| 4,979,949 A | 12/1990 | Matsen, III et al. | |
| 5,078,140 A | 1/1992 | Kwoh | |

(Continued)

FOREIGN PATENT DOCUMENTS

EP 0776738 A2 6/1997

(Continued)

OTHER PUBLICATIONS

Davies, BL, et al., "A Surgeon Robot for Prostatectomies," Center for Robotics, Imperial College of Science, *IEEE* (1991).

(Continued)

*Primary Examiner*—Pedro Philogene
(74) *Attorney, Agent, or Firm*—Vista IP Law Group LLP (57) ABSTRACT

A surgical instrument system for use in surgical procedures is disclosed. The surgical instrument system includes a guide assembly, a surgical tip assembly, and a drive unit. The guide assembly includes an elongated portion having a central axis of rotation, and a distal end that is positioned a radial distance away from the central axis. The surgical tip assembly may be attached to the guide assembly. The drive unit is coupled to the guide assembly for rotating the guide assembly and thereby rotating the surgical tip with respect to the central axis.

24 Claims, 6 Drawing Sheets

U.S. PATENT DOCUMENTS

| | | | |
|---|---|---|---|
| 5,086,401 | A | 2/1992 | Glassman et al. |
| 5,154,717 | A | 10/1992 | Matsen, III et al. |
| 5,184,601 | A | 2/1993 | Putman |
| 5,217,003 | A | 6/1993 | Wilk |
| 5,217,466 | A * | 6/1993 | Hasson ............... 606/119 |
| 5,236,432 | A | 8/1993 | Matsen, III et al. |
| 5,238,005 | A | 8/1993 | Imran |
| 5,299,288 | A | 3/1994 | Glassman et al. |
| 5,318,528 | A * | 6/1994 | Heaven et al. ........ 604/95.01 |
| 5,339,799 | A * | 8/1994 | Kami et al. ............ 600/117 |
| 5,350,355 | A | 9/1994 | Sklar |
| 5,368,015 | A | 11/1994 | Wilk |
| 5,372,147 | A | 12/1994 | Lathrop, Jr. et al. |
| 5,382,885 | A | 1/1995 | Salcudean et al. |
| 5,397,323 | A | 3/1995 | Taylor et al. |
| 5,398,691 | A | 3/1995 | Martin |
| 5,402,801 | A | 4/1995 | Taylor |
| 5,410,638 | A | 4/1995 | Colgate et al. |
| 5,417,210 | A | 5/1995 | Funda et al. |
| 5,448,989 | A * | 9/1995 | Heckele ............... 600/142 |
| 5,515,478 | A | 5/1996 | Wang |
| 5,524,180 | A | 6/1996 | Wang et al. |
| 5,540,649 | A | 7/1996 | Bonnell et al. |
| 5,553,198 | A | 9/1996 | Wang et al. |
| 5,572,999 | A | 11/1996 | Funda et al. |
| 5,618,294 | A * | 4/1997 | Aust et al. ............ 606/170 |
| 5,624,379 | A * | 4/1997 | Ganz et al. ............ 600/104 |
| 5,624,398 | A | 4/1997 | Smith et al. |
| 5,626,595 | A | 5/1997 | Sklar et al. |
| 5,631,973 | A | 5/1997 | Green |
| 5,632,758 | A | 5/1997 | Sklar |
| 5,649,956 | A | 7/1997 | Jensen et al. |
| 5,657,429 | A | 8/1997 | Wang et al. |
| 5,754,741 | A | 5/1998 | Wang et al. |
| 5,762,458 | A | 6/1998 | Wang et al. |
| 5,784,542 | A * | 7/1998 | Ohm et al. ............ 700/260 |
| 5,792,135 | A | 8/1998 | Madhani et al. |
| 5,800,333 | A | 9/1998 | Liprie |
| 5,800,423 | A | 9/1998 | Jensen |
| 5,807,282 | A * | 9/1998 | Fowler ............... 600/571 |
| 5,807,377 | A * | 9/1998 | Madhani et al. .......... 606/1 |
| 5,807,378 | A | 9/1998 | Jensen et al. |
| 5,808,665 | A | 9/1998 | Green |
| 5,810,880 | A | 9/1998 | Jensen et al. |
| 5,814,038 | A | 9/1998 | Jensen et al. |
| 5,815,640 | A | 9/1998 | Wang et al. |
| 5,817,084 | A | 10/1998 | Jensen |
| 5,821,920 | A | 10/1998 | Rosenberg et al. |
| 5,825,982 | A | 10/1998 | Wright et al. |
| 5,828,197 | A | 10/1998 | Martin et al. |
| 5,833,656 | A | 11/1998 | Smith et al. |
| 5,855,553 | A | 1/1999 | Tajima et al. |
| 5,855,583 | A * | 1/1999 | Wang et al. ............ 606/139 |
| 5,876,325 | A * | 3/1999 | Mizuno et al. .......... 600/102 |
| 5,878,193 | A | 3/1999 | Wang et al. |
| 5,907,664 | A | 5/1999 | Wang et al. |
| 5,931,832 | A | 8/1999 | Jensen |
| 5,954,692 | A | 9/1999 | Smith et al. |
| 5,971,976 | A | 10/1999 | Wang et al. |
| 5,976,122 | A | 11/1999 | Madhani et al. |
| 6,001,108 | A | 12/1999 | Wang et al. |
| 6,007,550 | A * | 12/1999 | Wang et al. ............ 606/139 |
| 6,024,695 | A | 2/2000 | Taylor et al. |
| 6,036,636 | A | 3/2000 | Motoki et al. |
| 6,063,095 | A | 5/2000 | Wang et al. |
| 6,080,181 | A | 6/2000 | Jensen et al. |
| 6,096,004 | A | 8/2000 | Meglan et al. |
| 6,102,850 | A | 8/2000 | Wang et al. |
| 6,106,511 | A * | 8/2000 | Jensen ............... 606/1 |
| 6,120,433 | A * | 9/2000 | Mizuno et al. .......... 600/102 |
| 6,132,368 | A | 10/2000 | Cooper |
| 6,132,441 | A | 10/2000 | Grace |
| 6,197,017 | B1 | 3/2001 | Brock et al. |
| 6,206,903 | B1 | 3/2001 | Ramans |
| 6,223,100 | B1 | 4/2001 | Green |
| 6,231,565 | B1 | 5/2001 | Tovey et al. |
| 6,233,504 | B1 | 5/2001 | Das et al. |
| 6,246,200 | B1 | 6/2001 | Blumenkranz et al. |
| 6,290,675 | B1 | 9/2001 | Vujanic et al. |
| 6,309,397 | B1 | 10/2001 | Julian et al. |
| 6,312,435 | B1 | 11/2001 | Wallace et al. |
| 6,325,808 | B1 | 12/2001 | Bernard et al. |
| 6,331,181 | B1 | 12/2001 | Tierney et al. |
| 6,346,072 | B1 | 2/2002 | Cooper |
| 6,364,888 | B1 | 4/2002 | Niemeyer et al. |
| 6,371,907 | B1 | 4/2002 | Hasegawa et al. |
| 6,375,471 | B1 | 4/2002 | Wendlandt et al. |
| 6,377,011 | B1 | 4/2002 | Ben-Ur |
| 6,385,509 | B2 | 5/2002 | Das et al. |
| 6,394,998 | B1 | 5/2002 | Wallace et al. |
| 6,398,726 | B1 | 6/2002 | Ramans et al. |
| 6,432,112 | B2 | 8/2002 | Brock et al. |
| 6,436,107 | B1 | 8/2002 | Wang et al. |
| 6,441,577 | B2 | 8/2002 | Blumenkranz et al. |
| 6,451,027 | B1 | 9/2002 | Cooper et al. |
| 6,459,926 | B1 | 10/2002 | Nowlin et al. |
| 6,463,361 | B1 | 10/2002 | Wang et al. |
| 6,468,265 | B1 | 10/2002 | Evans et al. |
| 6,490,490 | B1 | 12/2002 | Uchikubo et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,496,099 | B2 | 12/2002 | Wang et al. |
| 6,517,565 | B1 | 2/2003 | Whitman et al. |
| 6,522,906 | B1 | 2/2003 | Salisbury, Jr. et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,594,552 | B1 | 7/2003 | Nowlin et al. |
| 6,620,173 | B2 | 9/2003 | Gerbi et al. |
| 6,645,196 | B1 | 11/2003 | Nixon et al. |
| 6,676,684 | B1 | 1/2004 | Morley et al. |
| 6,685,698 | B2 | 2/2004 | Morley et al. |
| 6,692,485 | B1 | 2/2004 | Brock et al. |
| 6,699,235 | B2 | 3/2004 | Wallace et al. |
| 6,720,988 | B1 | 4/2004 | Gere et al. |
| 6,726,675 | B1 | 4/2004 | Beyar |
| 6,726,699 | B1 | 4/2004 | Wright et al. |
| 6,728,599 | B2 | 4/2004 | Wang et al. |
| 6,770,081 | B1 | 8/2004 | Cooper et al. |
| 6,783,524 | B2 | 8/2004 | Anderson et al. |
| 6,788,018 | B1 | 9/2004 | Blumenkranz |
| 6,793,653 | B2 | 9/2004 | Sanchez et al. |
| 6,799,065 | B1 | 9/2004 | Niemeyer |
| 6,817,972 | B2 | 11/2004 | Snow |
| 6,817,974 | B2 | 11/2004 | Cooper et al. |
| 6,837,883 | B2 | 1/2005 | Moll et al. |
| 6,840,938 | B1 | 1/2005 | Morley et al. |
| 6,852,107 | B2 | 2/2005 | Wang et al. |
| 6,860,877 | B1 | 3/2005 | Sanchez et al. |
| 6,911,916 | B1 | 6/2005 | Wang et al. |
| 6,936,001 | B1 | 8/2005 | Snow |
| 6,951,535 | B2 | 10/2005 | Ghodoussi et al. |
| 6,963,792 | B1 | 11/2005 | Green |
| 6,994,708 | B2 | 2/2006 | Manzo |
| 7,025,064 | B2 * | 4/2006 | Wang et al. ............ 128/898 |

FOREIGN PATENT DOCUMENTS

| | | |
|---|---|---|
| JP | 06114000 | 4/1994 |
| WO | WO98/25666 | 6/1998 |
| WO | WO 00/60521 | 10/2000 |
| WO | WO 00/67640 | 11/2000 |

| WO | WO 02/74178 | 2/2002 |

OTHER PUBLICATIONS

Kwoh, Y. S., et al., "Robot with Improved Absolute Positioning Accuracy for CT Guided Stereotactic Brain Surgery," *IEEE Transactions on Biomedical Engineering*, 35(2) (1998).

Dohi, T., "Medical Application of Robotics Mechatronics," *International Biomedical Engineering Days*, (1992).

Sabatini, A.M., et al., "Force Feedback-Based Telemicromanipulation for Robot Surgery on Soft Tissue," *IEEE Engineering in Medicine & Biology Society*, (1998).

Ikuta, et al., "Shape Memeory Alloy Servo Actuator System With Electric Resistance Feedback and Application for Active Endoscope," 1988 *IEEE*, CH2555-1-88/0000/0427-430.

M. W. Thring, "Robots and Telechirs: Manipulators With Memory; Remote Manipulators; Machine Limbs for the Handicapped," First published in 1983 by Ellis Horwood Limited.

EPO Communication dated Dec. 27, 2007 for related European application serial No. 00 928 917.4-1526, filed May 9, 2000; Applicant: Hansen Medical, Inc. (4 pages).

* cited by examiner

SURGICAL INSTRUMENT

RELATED APPLICATIONS

This application is a continuation of U.S. application Ser. No. 09/783,637, filed Feb. 14, 2001 now abandoned which is a continuation of PCT US/00/12553 filed May 9, 2000 which designates U.S., which claims the benefit of U.S. Provisional Application No. 60/133,407, filed May 10, 1999. The entire teachings of the above applications are incorporated by reference.

BACKGROUND OF THE INVENTION

The invention relates generally to surgical instruments and particularly relates to computer controlled or assisted surgical instruments. Computer controlled or assisted surgical instrumentation typically involves the manual manipulation of instruments such as scalpels, scissors or catheters during surgical procedures with the aid of a computer. The computer may guide the movement of the instrument, may assist a surgeon in moving the instrument, or may simply monitor the movement of the instrument. The present invention is particularly useful in systems in which the movement a surgeon's hand is used to indirectly control the movement of the instrument via mechanical couplings and transmissions. As surgical instruments become more sophisticated, many of these devices will be monitored and possibly further controlled by computers.

Computer controlled surgical instrumentation has many advantages over conventional devices. For example, computer enhanced systems may coordinate many complex motions—more than is possible for the unaided human. These systems may scale motion arbitrarily, remove tremor, provide safe zones and limit forces. Computer systems may perform movement "macros" or stereotypical motion, such as suturing or knot typing. Even feedback processes, such as maintaining a constant grasp or probing for occlusions may be possible with advanced computer controlled surgical instruments.

Computer controlled instrumentation is particularly effective for minimally invasive surgical procedures, since access and visualization are severely limited. Minimally invasive techniques involve operating through small—typically 5 mm to 10 mm diameter—incisions, through which instruments are inserted. A video camera may also be inserted into the patient in order to view the operative site. Minimally invasive surgery is typically less traumatic than conventional surgery due, in part, to the significant reduction in incision size. Furthermore, hospitalization is reduced and recovery periods shorten as compared with convention techniques.

Although the surgeon has visual feedback from the surgical site, from either a camera, radiological imaging or ultrasonic scanning, the ability to control the relatively simple laparoscopic instruments remains difficult. Even with good visual feedback, the surgeon's tactile and positional sense are physically removed from the operative site rendering endoscopic procedures slow and clumsy.

Current instrumentation, with forceps, scissors, etc., inserted into the body at the end of long slender push rods is not fully satisfactory. The use of such conventional instrumentation increases operative time, and potentially heightens risk. For example, tissue may be injured when the laparoscopic tool moves outside the visual field. Moreover, there are limitations on the type and complexity of procedures that may be performed laparoscopically due, in part, to the limitations on the instruments that are used.

Development work has been undertaken to investigate the use of robots in surgery. Typically, these robotic systems use arms that reach over the surgical table and manipulate surgical instruments in a manner similar to the human operator. The presence of such a robot at the surgical site, however, may be problematic if the robot is too large or otherwise impedes access to the patient during surgery.

There is a need, therefore, for a surgical instrument that provides computer assistance yet does not impede access to the patient during surgery.

There is further a need for such a system that may be used for minimally invasive surgery.

SUMMARY OF THE INVENTION

The invention provides a surgical instrument system for use in surgical procedures. The surgical instrument system includes a guide assembly, a surgical tip assembly, and a drive unit. The guide assembly includes an elongated portion having a central axis of rotation, and a distal end that is positioned a radial distance away from the central axis. The surgical tip assembly may be attached to the guide assembly. The drive unit is coupled to the guide assembly for rotating the guide assembly and thereby rotating the surgical tip with respect to the central axis. In an embodiment, the surgical tip assembly includes a surgical manipulator that provides four degrees of freedom, and the guide assembly includes a tube having a curve at its distal end.

BRIEF DESCRIPTION OF THE DRAWINGS

The following description may be further understood with reference to the accompanying drawings in which.

The drawings are for illustrative purposes only and are not to scale.

DETAILED DESCRIPTION OF THE ILLUSTRATED EMBODIMENTS

The present invention provides an instrument system that may be used to perform minimally invasive surgery. An exemplary system of the invention is actuated by a flexible cable assembly as shown in FIGS. 1-9. Generally, the cable assembly is in the form of an array, and is removably attached to an actuation drive unit. The actuation drive unit is remote from the operative site and is preferably positioned a distance away from the sterile field. The drive unit is electrically controlled by a computer system that is connected to a user interface. Commands issued at the user interface are translated by the computer into electronically driven motion in the drive unit. The surgical instrument, which is tethered to the drive unit through its cable connection, produces the desired motion.

The surgical instrument is generally composed of two components—a surgical adaptor and an instrument insert. The surgical adaptor is a passive mechanical device, driven by the attached cable array. Since the surgical adaptor is detachable and relatively simple, it may be designed for particular surgical applications, such as abdominal, cardiac, spinal, arthroscopic, sinus, neural, etc. The surgical insert couples to the adaptor and essentially provides a means for exchanging the instrument end-effectors. These inserts may include forceps, scissors, needle drivers, electrocautery, etc.

Figure 1:
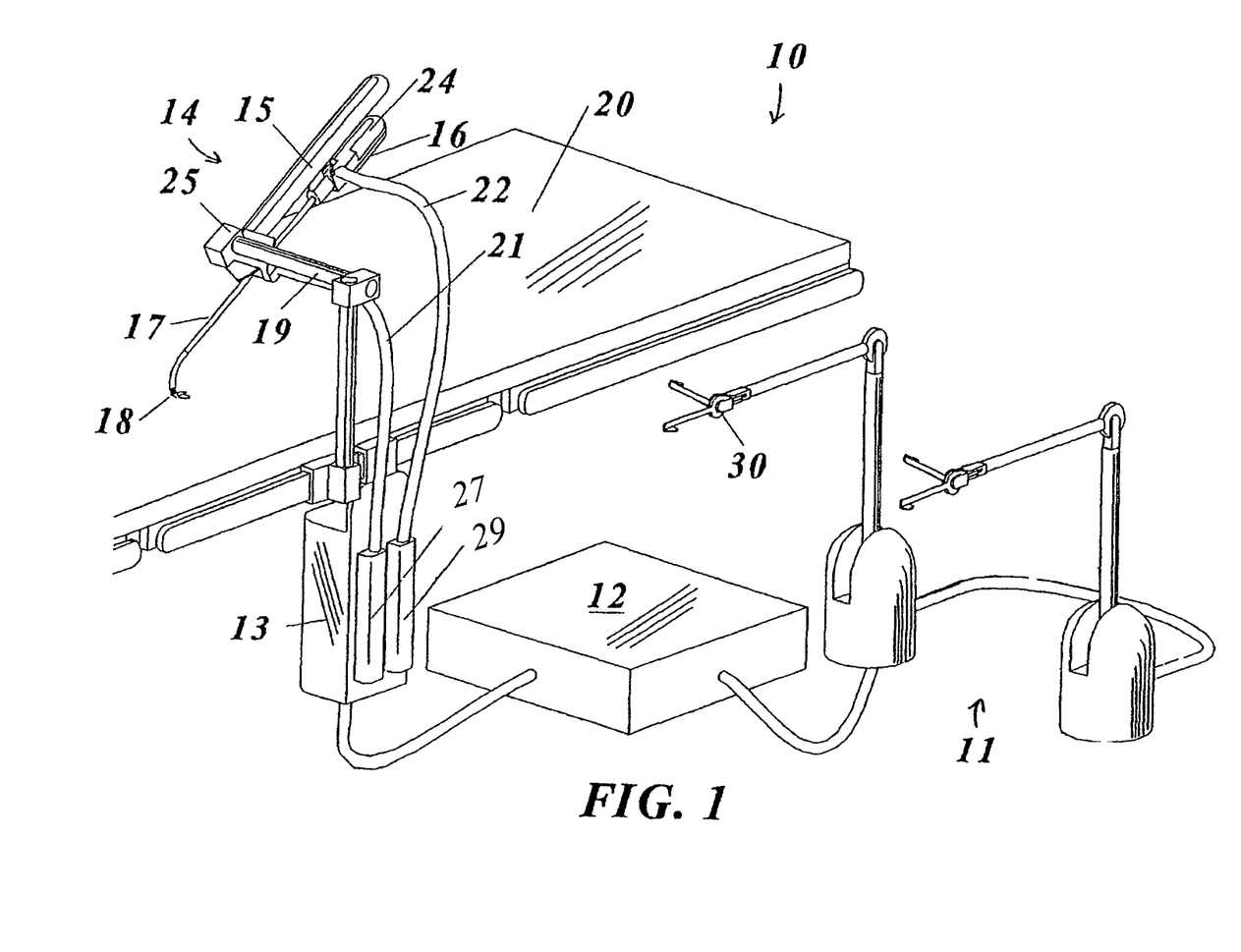
FIG. 1 shows a perspective view of a minimally invasive surgical system including a surgical instrument of the present invention.

Referring specifically to FIG. 1, a surgical instrument system 10 may preferably be used to perform minimally invasive procedures, although it is to be understood that the system may be used to perform other procedures as well, such as open or endoscopic surgical procedures. The system 10 includes a surgeon's interface 11, computation system 12, drive unit 13 and a surgical instrument 14. The surgical instrument 14 is comprised of a surgical adaptor 15 and instrument insert 16. The system may be used by positioning the end effector 18 of the instrument insert 16, which is inserted through the surgical adaptor 15. During use, a surgeon may manipulate the handle 30 of the surgeon's interface 11, to effect desired motion of the end effector 18 within the patient. The movement of the handle 30 may be interpreted by the computation system 12 to enhance the movement of the end effector.

The system may also include an endoscope with a camera to remotely view the operative site. The camera may be mounted on the distal end of the instrument insert, or may be positioned away from the site to provide additional perspective on the surgical operation. In certain situations, it may be desirable to provide the endoscope through an opening other than the one used by the surgical adaptor 15.

The surgical adaptor 15 of the surgical instrument 14 includes two mechanical cable-in-conduit bundles 21 and 22. These cable bundles 21 and 22 terminate at two connection modules 27 and 29, which removably attach to the drive unit 13. Although two cable bundles are described here, it is to be understood that more or fewer cable bundles may be used. The drive unit 13 is preferably located outside the sterile field, although it may draped with a sterile barrier so that is may be operated within the sterile field.

In the preferred method to setup the system, the surgical instrument 14 is inserted into the patient through an incision or an opening. The instrument 14 is then mounted to the rigid post 19 using a mounting bracket 25. The cable bundles 21 and 22 are then passed away from the operative area to the drive unit 13. The connection modules 27 and 29 of the cable bundles 21 and 22 are then engaged onto the actuation unit 13. Instrument inserts 16 may then be passed through the surgical adaptor 15. The surgical inserts 16 are coupled laterally with the surgical adaptor 15 through the adaptor coupler 24.

The instrument 14 is controlled by the interface handle 30, which may be manipulated by the surgeon. Movement of the handle may produce proportional movement of the instrument 14 through the coordinating action of the computation system 12. In the typical case, movement of a single hand controls movement of a single instrument. FIG. 1, shows a second handle that may be employed to control an additional instrument.

The surgeon's interface 30 is in electrical communication with the computation system 12, and the computation system 12 is in electrical communication with the actuation unit 13. The actuation unit 13, however, is in mechanical communication with the instrument 14. The mechanical communication with the instrument allows the electromechanical components to be removed from the operative region, and preferably from the sterile field. The surgical instrument 14 provides a number of independent motions, or degrees-of-freedom, to the end effector 18. These degrees-of-freedom are provided by both the surgical adaptor 15 and the instrument insert 16.

Figure 2:
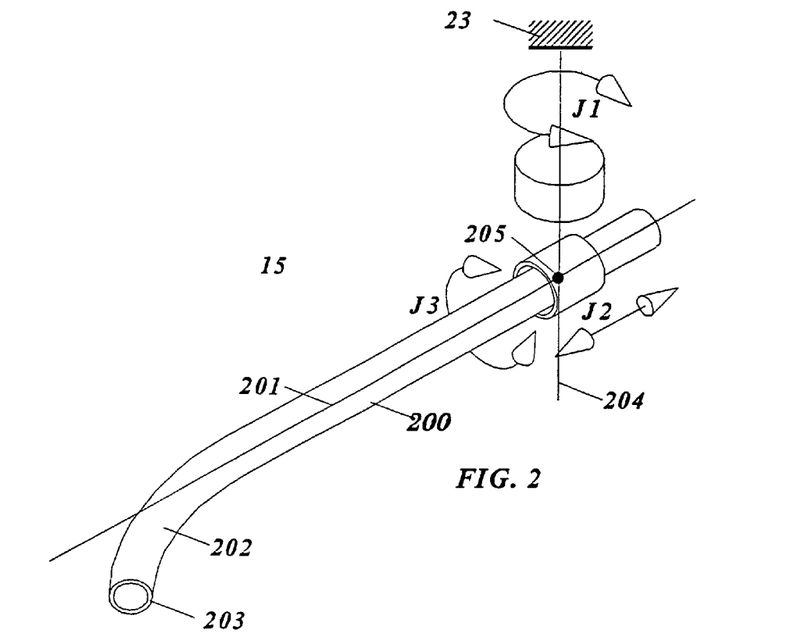
FIG. 2 shows a functional schematic diagram of the surgical adaptor component of the system of FIG. 1.

The surgical adaptor 15, shown schematically in FIG. 2, provides three degrees-of-freedom, which are achieved using a pivotal joint J1, a linear joint J2, and a rotary joint J3. From the mounting bracket 23, shown in schematically FIG. 2, a pivotal joint J1 pivots the surgical adaptor assembly about a fixed axis 204. A first linear joint J2, moves the guide tube 200 along an axis 201 defined by the tube. A rotary joint J3 rotates the guide tube 200 its long axis 201. The guide tube 200 has a bend 202 that causes the distal end of the tube to orbit the axis 201 when the guide tube is rotated about its axis.

Through a combination of movements at joints J1-J3, the surgical adaptor 15 can position its distal end 203 to any desired position in three-dimensional space. By using only a single pivotal motion, the external motion of the surgical adaptor 15 is minimized. Furthermore, the pivotal axis 204 and the longitudinal axis 201 intersect at a fixed point 205. At this fixed point 205, the lateral motion of the guide tube 200 is essentially zero.

Figure 3:
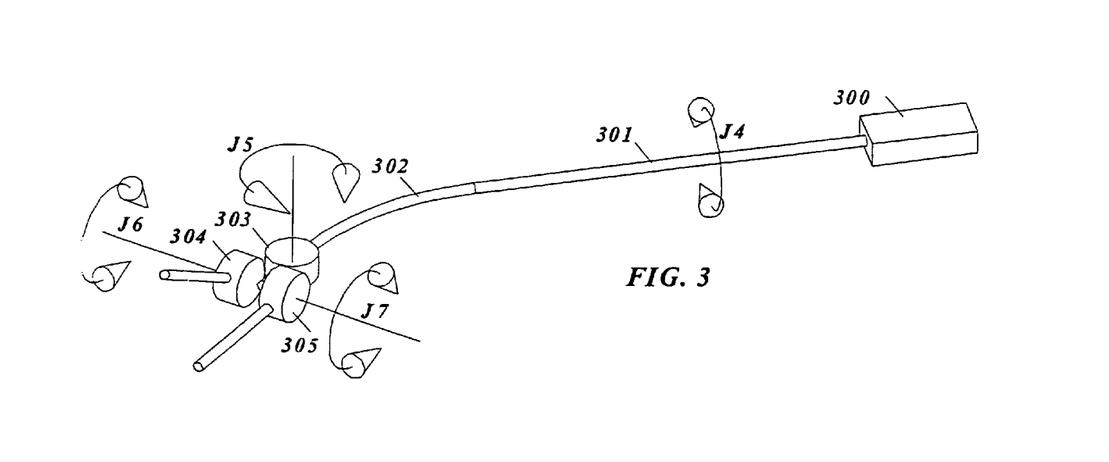
FIG. 3 shows a functional schematic diagram of the instrument insert component of the system of FIG. 1.

FIG. 3 shows a schematic representation of the kinematics of the instrument insert 16. The instrument insert 16 is placed through the surgical adaptor 15, so that the movements of the insert are added to those of the adaptor. The instrument insert 16 has two grips 304 and 305, which are rotatably coupled to wrist link 303 by two-rotary joints J6 and J7. The axes of joints J6 and J7 are essentially collinear. The wrist link 303 is coupled to a flexible shaft 302 through a rotary joint J5, whose axis is essentially orthogonal to the axes of joints J6 and J7. The flexible shaft 302 is attached to a rigid shaft 301. The rigid shaft 301 is rotatably coupled by a joint J4 to the instrument insert base 300. The axis of joint J4 is essentially co-axial with the rigid shaft 301.

The combination of joints J4-J7 allow the instrument insert 16 to be actuated with four degrees-of-freedom. When coupled to the surgical adaptor 15, the insert and adaptor provide the surgical instrument 14 with seven degrees-of-freedom. Although four degrees-of-freedom are described here for the insert 16, it is to be understood that greater and fewer numbers of degrees-of-freedom are possible with different instrument inserts. For example, an energized insert with only one gripper may be useful for electro-surgery applications, while an insert with an additional linear motion may provide stabling capability.

Figure 4:
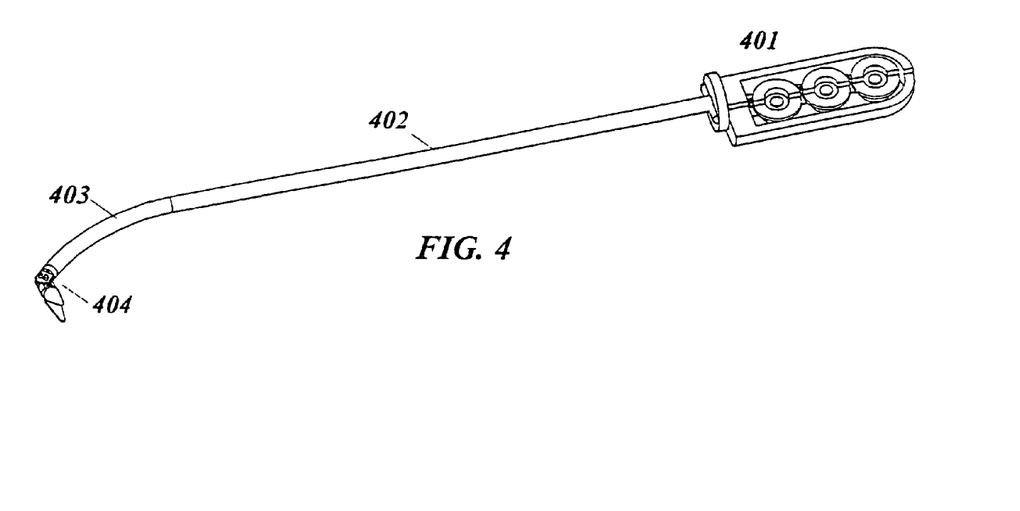
FIG. 4 shows a perspective view of the surgical instrument insert component of the system of FIG. 1.

The instrument insert 16, shown in FIG. 4, is comprised of a coupler 401, a rigid stem 402, a flexible section 403 and an end effector 404. The coupler 401 includes one or more wheels 405 which laterally engage wheels 726 of the coupler section 700 on the surgical adaptor 15. The coupler 401 also includes an axial wheel 406, which also engages a wheel on the adaptor. The axial engagement wheel 406 is fixed to the rigid stem 402, and is used to rotate the end-effector axially at the distal end of the flexible section.

Figure 5:
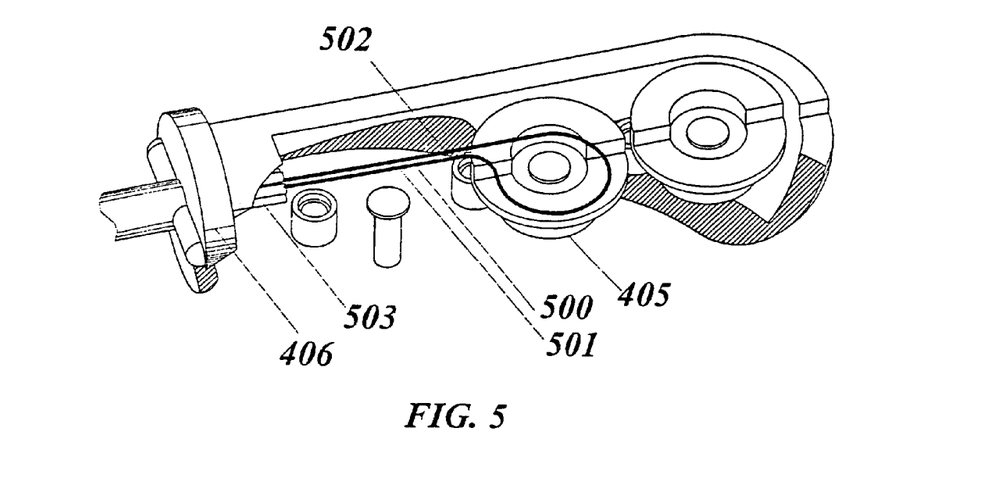
FIG. 5 shows a perspective view of the coupler component of the system of FIG. 1.

A detail of the coupler assembly 401 is shown in FIG. 5. Each wheel 405 of the coupler has two cables 500 and 501 that are affixed to the wheel and wrapped about opposite sides at its base. The lower cable 500 also rides over an idler pulley 502, which routes the cables toward the center of the instrument stem 402. It is desirable to maintain the cables near the center of the instrument stem, since the cables will in accordance with the rotation of the stem. The closer the cables are to the central axis of stem the less disturbance motion on the cables. The cables are then routed through plastic tubes 503 that are affixed to the proximal end of the rigid stem 402 and the distal end of the flexible section 403. The tubes maintain constant length pathways for the cables as they move within the instrument stem.

Figure 6A:
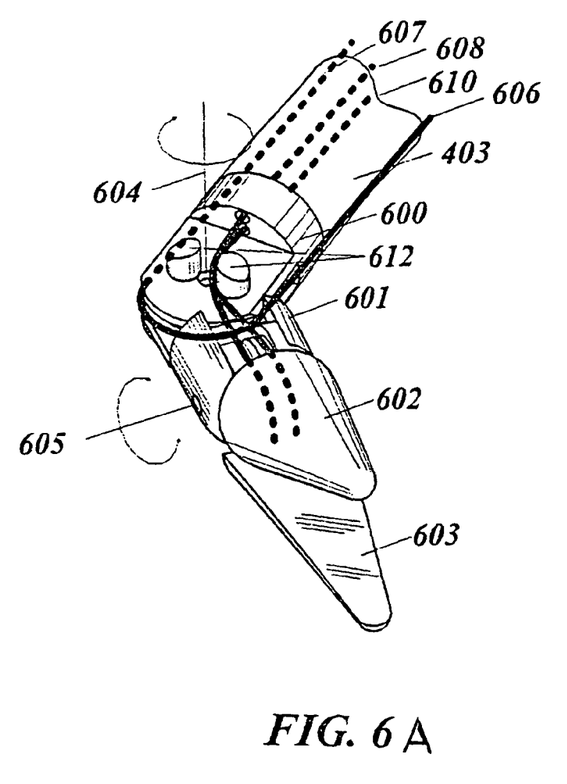
FIG. 6A-6B show perspective views of the end-effector component of the system of FIG. 1.
Figure 6B:
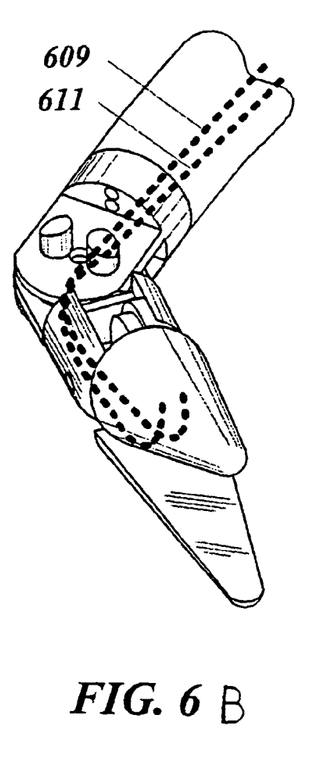

The end effector, shown in FIGS. 6A and 6B, is comprised of four members, a base 600, link 601, upper grip 602 and lower grip 603. The base 600 is affixed to the flexible section of the insert stem 403. The link 601 is rotatably connected to the base 600 about axis 604. The upper and lower grips 602 and 603 are rotatably connected to the link about axis 605, where axis 605 is essentially perpendicular to axis 604.

Six cables 606-611, shown schematically in FIG. 6A, actuate the four members 600-603 of the end effector. Cable 606 travels through the insert stem and through a hole in the base 600, wraps on a rounded surface on link 601, and then attaches on link 601. Tension on cable 606 rotates the link 601, and attached upper and lower grips 602 and 603, about axis 604. Cable 607 provides the opposing action to cable 606, and goes through the same routing pathway, but on the oppose side of the insert.

Cables 608 and 610 also travel through the stem 403 and through holes in the base 600. The cables 608 and 610 then pass between two fixed posts 612. These posts constrain the cables to pass substantially through the axis 604, which defines rotation of the link 601. This construction essentially allows free rotation of the link 601 with minimal length changes in cables 608-611. In other words, the cables 608-611, which actuate the grips 602 and 603, are essentially decoupled from the motion of link 601. Cables 608 and 610 pass over rounded sections and terminate on grips 602 and 603, respectively. Tension on cables 608 and 610 rotate grips 602 and 603 counter-clockwise about axis 605. Finally, as shown in FIG. 6B, the cables 609 and 611 pass through the same routing pathway as cables 608 and 610, but on the oppose side of the instrument. These cables 609 and 611 provide the clockwise motion to grips 602 and 603, respectively.

Figures 7A, 7B, 7C:
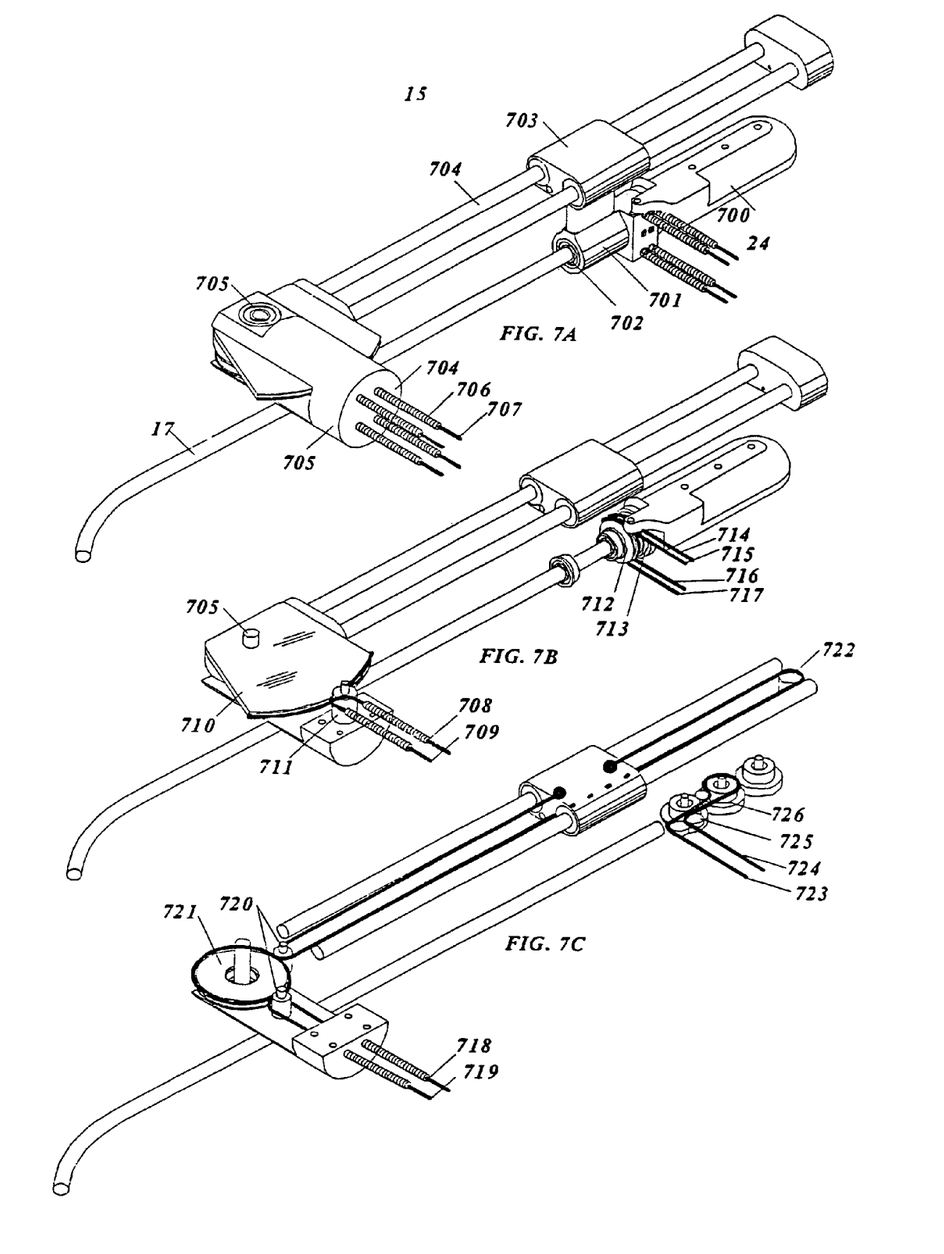
FIG. 7A-7C show exploded perspective views of the surgical instrument adaptor component of the system of FIG. 1.

The instrument 16 slides through the guide tube 17 of the adaptor 15, and laterally engages the adaptor coupler 24, as shown in FIGS. 7A-7C. The adaptor coupler 24 is pivotally mounted 700 to the guide tube housing 701. The guide tube housing 701 rotationally mounts the guide tube 17. The guide tube housing 701 is affixed to the linear slider 703, which travels along the linear stage 704. The linear stage 704 is pivotally mounted 705 on the base 706.

Cables, which enters the structure through conduits 707, actuate the adaptor 15. The base pivotal joint 705 is control by two cables 708 and 709, which pass over an idler pulley 711 and along opposing directions on base capstan 710. The guide tube capstan 712, affixed to the guide tube 17, and is actuated by cables 715 and 717, which differentially rotates the guide tube. The axial capstan 713 is rotationally coupled to the guide tube and is actuated by cables 716 and 718. The axial capstan 713 engages the axial engagement wheel 406 on the instrument.

The cables 718 and 719, shown in FIG. 7C, actuate the linear slider 703. The cables enter the base 705 through conduits 706 and around idler pulleys 720 and 721. Cable 718 passes freely through the linear slider 703 and around the distal idler pulley 722 and back toward the linear slider 703 onto which it terminates. The cable 719 terminates on the linear slider directly. The engagement wheels 726 located in the adaptor coupler 24 are actuated by cables which enter the pivotal adaptor coupler 700 guided by idler pulleys 725.

Figure 8:
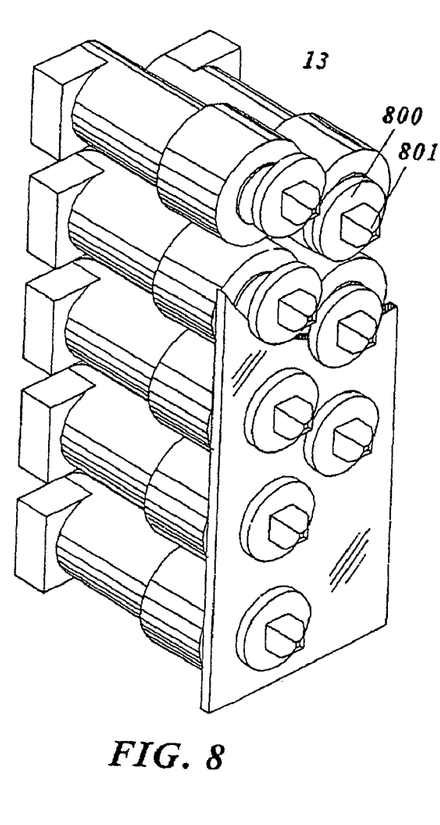
FIG. 8 shows a perspective view of the modular drive unit used in the system of FIG. 1.
Figure 9:
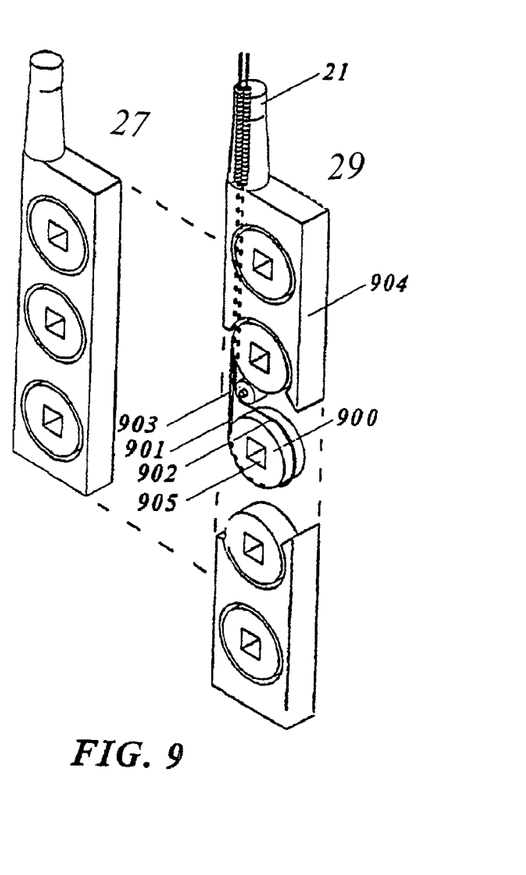
FIG. 9 shows detailed drawings of the connector components of the surgical adaptor used in the system of FIG. 1.

All of the cables in their individual conduits are collected into two bundles 21 and 22 that exit the adaptor. These cable bundles terminate on connection modules 27 and 29, which are shown in FIG. 9, and removably attach to the motor drive unit 13 (shown in FIG. 8). Each of the connection modules 27 and 29 contains a row of rotatable wheels 900, which engage matching wheels 800 located on the motor drive unit 13. As shown in FIG. 9, each wheel 900 actuates two cables 901 and 902, which wrap about the circumference in opposing directions. An idler pulley 903 aligns one of the cables 902, so that both cables 901 and 902 are in parallel and close together, so that they may be easily fitted into the cable bundle 21.

The connection modules 27 and 29 removably attach to the motor drive unit 13. Each wheel of each of the connection module matches, and is individually actuated by, the corresponding motor drive wheel 800. Notice that the square key 801 on the motor drive wheel matches the detent in the connection module wheel. Each motor drive wheel is fitted to the axle of an electrical motor 802.

With the instrument insert coupled to the surgical adaptor and the connection module fitted to the drive unit, the transmission allows each motor 802 to actuate a single degree-of-freedom in either the adaptor or the insert. The mechanical assembly thus allows decoupled motion for each degree of freedom. The complete system provides a full seven degrees-of-freedom of motion for the surgical instrument within the body. These degrees-of-freedom include three translational movements in three-dimensional space, three rotational movements allowing arbitrary orientation, and a single grip degree-of-freedom.

It is contemplated that various changes and modifications may be made to the drive unit, cable assembly, surgical adaptor or instrument insert without departing from the spirit and scope of the invention as define by the following claims and their equivalents.

What is claimed is:

1. A surgical instrument system for use in surgical procedures, said surgical instrument system including:
   a guide tube including an elongated portion having a central axis of rotation, a central opening along a longitudinal length of the guide tube, and a pre-shaped curved distal portion;
   a surgical tip configured for being inserted into the proximal end of the guide tube, passed through the central opening of the guide tube, and deployed out of the curved distal portion of the guide tube; and
   a drive unit including an electric motor having an output shaft coupled to the guide tube configured for rotating the guide tube with respect to the central axis of rotation in response to control signals through a user input device.

2. The surgical instrument system of claim 1, wherein the curved distal portion of the guide tube is rigid.

3. The surgical instrument system of claim 1, wherein the surgical tip is removably insertable into the guide tube.

4. The surgical instrument system of claim 1, wherein the drive unit is also configured for moving the surgical tip within at least three degrees of freedom.

5. The surgical instrument system of claim 1, wherein the drive unit is also configured for actuating the surgical tip.

6. The surgical instrument system of claim 1, wherein the surgical tip includes an end effector having opposing grip portions.

7. The surgical instrument system of claim 1, wherein the drive unit is configured for positioning the curved distal portion of the guide tube in three-dimensional space by pivoting the guide tube only in a single plane and rotating the guide tube relative to the central axis.

8. The surgical system of claim 1, further comprising:
a surgical insert to which the surgical tip is coupled;
a first coupler mounted to the proximal end of the guide tube, and
a second coupler mounted to a proximal end of the surgical insert, wherein the second coupler is configured for mating with the first coupler, and the drive unit is configured for being coupled to the first coupler.

9. A surgical instrument system for use in surgical procedures, said surgical instrument system including:
a surgical instrument comprising:
a guide tube including a proximal end and a distal end having a pre-shaped curved portion, and a central opening along a longitudinal length of the guide tube, the guide tube being configured for insertion into a patient; and
a surgical insert having an end effector that may be used in surgical procedures, the end effector configured for being inserted into the proximal end of the guide tube, passed through the central opening of the guide tube, and deployed out of the curved portion of the guide tube within the patient; and
a drive unit including an electric motor having an output shaft coupled to the surgical instrument for translating the surgical instrument along a longitudinal axis of the surgical instrument in response to control signals generated through a user input device.

10. The surgical system of claim 9, wherein the drive unit is also configured for rotating the guide tube with respect to the central axis of the guide tube within the patient.

11. The surgical system of claim 9, wherein the drive unit is also configured for manipulating the surgical insert relative to the guide tube within the patient.

12. The surgical system of claim 9, wherein the drive unit is also configured for actuating the end effector.

13. The surgical system of claim 9, wherein the drive unit is configured to manipulate the surgical instrument in least three degrees-of-freedom.

14. The surgical system of claim 9, wherein the end effector includes two opposing gripper portions for use in surgical procedures.

15. The surgical system of claim 9, further comprising:
a user interface for receiving user commands;
a computer processing unit coupled to the user interface for translating the user commands into electronic signals, wherein the drive unit is coupled to the computer processing unit for manipulating the surgical instrument in accordance with the electronic signals.

16. The surgical system of claim 15, wherein the user interface comprises at least one handle that can be manipulated by the user to provide the user commands.

17. The surgical system of claim 9, wherein the surgical instrument comprises a linear stage and a linear slider on which the guide tube is mounted.

18. The surgical system of claim 9, wherein the drive unit is configured for positioning the distal end of the guide tube in three-dimensional space by pivoting the guide tube only in a single plane and rotating the guide tube relative to the central axis.

19. A surgical instrument system for use in surgical procedures, said surgical instrument system including:
a surgical instrument comprising:
a guide tube including a proximal end and a distal end having a pre-shaped curved portion, and a central opening along a longitudinal length of the guide tube, the guide tube being configured for insertion into a patient; and
a surgical insert having an end effector that may be used in surgical procedures, the end effector configured for being inserted into the proximal end of the guide tube, passed through the central opening of the guide tube, and deployed out of the curved portion of the guide tube within the patient; and
a drive unit having one or more electric motors configured for manipulating the surgical instrument within at least one-degree-of freedom within the patient in response to control signals generated by a user input device,
wherein the curved distal portion of the guide tube is rigid.

20. A method of manipulating a surgical instrument, comprising the steps of:
inserting a pre-shaped curved distal portion of a guide tube into a patient;
inserting an end effector of a surgical insert into a proximal end of the guide tube, passing the end effector through a central opening of the guide tube, and deploying the end effector out of the curved distal portion of the guide tube within the patient to form a surgical instrument;
removably securing the surgical instrument in a surgical environment;
operating an electrical drive unit to effect a rotation of the curved distal portion of the guide tube relative to a central axis of the guide tube; and
actuating the end effector to perform a medical procedure in the patient.

21. A surgical instrument system for use in surgical procedures, said surgical instrument system including:
a surgical instrument comprising:
a guide tube including a proximal end and a distal end having a pre-shaped curved portion, and a central opening along a longitudinal length of the guide tube, the guide tube being configured for insertion into a patient; and
a surgical insert having an end effector that may be used in surgical procedures, the end effector configured for being inserted into the proximal end of the guide tube, passed through the central opening of the guide tube, and deployed out of the curved portion of the guide tube within the patient; and
a drive unit having one or more electric motors configured for manipulating the surgical instrument within at least one-degree-of freedom within the patient in response to control signals generated by a user input device,
wherein the surgical instrument comprises a first coupler mounted to the proximal end of the guide tube, and a second coupler mounted to a proximal end of the surgical insert, and wherein the second coupler is configured for mating with the first coupler, and the drive unit is configured for being coupled to the first coupler.

22. The method of claim 20, further comprising positioning the curved distal portion of the guide tube in three-dimensional space by pivoting the surgical instrument in a single plane and rotating the surgical instrument relative to the central axis.

23. The method of claim 20, wherein the end effector actuation step is accomplished using the electrical drive unit.

24. A method of manipulating a surgical instrument, comprising the steps of:
inserting a pre-shaped curved distal portion of a guide tube into a patient;
inserting an end effector of a surgical insert into a proximal end of the guide tube, passing the end effector through a central opening of the guide tube, and deploying the end effector out of the curved distal portion of the guide tube within the patient to form a surgical instrument;

removably securing the surgical instrument in a surgical environment;

rotating the curved distal portion of the guide tube relative to a central axis of the guide tube;

actuating the end effector to perform a medical procedure in the patient; and operating an electrical drive unit to effect at least one of the guide tube rotation and the end effector actuation steps; wherein the surgical instrument comprises a first coupler mounted to the guide tube and a second coupler mounted to the surgical insert, the method further comprising mating the first and second couplers together, and coupling the drive unit to the second coupler, wherein operation of the drive unit effects the at least one of the surgical instrument rotation and the end effector actuation steps via the second coupler.

* * * * *